US00PP13747P39

(12) United States Plant Patent
Zerr

(10) Patent No.: US PP13,747 P3
(45) Date of Patent: Apr. 29, 2003

(54) POINSETTIA PLANT NAMED 'FISLEMON'

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/850,076

(22) Filed: May 8, 2001

(65) Prior Publication Data

US 2002/0059666 P1 May 16, 2002

(51) Int. Cl.[7] ..... A01H 5/00

(52) U.S. Cl. ..... Plt./305

(58) Field of Search ..... Plt./305

*Primary Examiner*—Bruce R. Campell
*Assistant Examiner*—Michelle Kizilkaya
(74) *Attorney, Agent, or Firm*—Foley & Lardner

(57) ABSTRACT

A new and distinct cultivar of Poinsettia plant named 'Fislemon', as described and illustrated, and particularly characterized by the combined features of light yellow, uniform bract color; medium sized inflorescence with weakly lobed bracts; uniform dark-green, distinctly lobed foliage; medium sized plant habit, well-branched and relatively wide; and early flowering response.

1 Drawing Sheet

LATIN NAME OF THE GENUS AND SPECIES OF THE PLANT CLAIMED

*Euphorbia pulcherrima*

VARIETY DENOMINATION

Fislemon

BACKGROUND OF THE INVENTION

The present invention relates to a new and distinct cultivar of Poinsettia plant known by the cultivar name 'Fislemon', and botanically known as *Euphorbia pulcherrima.*

'Fislemon' is a product of a planned breeding program which had the objective of creating new Poinsettia cultivars with white or yellow flower color in combination with dark-green foliage and good cultivation ability.

'Fislemon' originated from a hybridization made by the inventor, Katharina Zerr, in Hillscheid, Germany, in 1996. The female parent was a propietary hybrid seedling, no. S90-602-1 (unpatented), characterized by salmon-pink bract color, medium green foliage, and medium sized, wide and bushy plant habit. The male parent was a hybrid seedling, no. S90-502-1 (unpatented), having red bract color, dark green foliage, and early flowering.

The seeds germinated in the spring of 1997, and the resulting seedlings were identified by numbers. In the summer of 1997, a cutting was taken from each seedling, rooted and grown out for examination as flowering single-stem plants. 'Fislemon' was discovered and selected as one flowering plant no. 6935 within the progeny of the stated cross/parentage by Katharina Zerr in the fall of 1997. After this plant had been chosen, more cuttings were taken from the original seedling and grafted on rootstocks of the variety 'Beckmann's Altrosa' (U.S. Plant Pat. No. 9,336), in order to transmit the branching causing agent, phytoplasma, into the clone to improve the branching causing characteristics. From the upper area of the successfully grafted plants,

DETAILED BOTANICAL DESCRIPTION

The plants described were grown in a greenhouse in Hillscheid, Germany, in the fall of 1999. Rooted cuttings were planted into 14 cm pots on July 23, and were pinched 12 days after that, leaving 8 nodes. The minimum temperature was about 20° C. until the end of September, and about 17–18° C. thereafter. The plants initiated flowers under natural short-day conditions in fall.

Observations and measurements were mainly taken at the beginning of full flowering. In the following description color references are made to The Royal Horticultural Society Colour Chart (R.H.S.). The color values were determined indoors in a north light.

Plant:

*Form.*—Shrub, self-branching.
*Growth habit.*—Moderately compact, medium height pinched plants are bushy and wide in shape.
*Height* (*above soil line*).—32.5 cm.
*Width.*—55 cm.
*Average number of branches.*—7–9.
*Average length of branches.*—24–26 cm.
*Stem color.*—Light green, RHS 143 C.
*Internodes.*—35 mm in length.
*Rooting.*—Fast to medium, less than 20 days.
*Blooming habit.*—Begin under natural short day conditions in fall; botanically (cyathia open) in early December; commercially (bracts colored, marketable) in late November.
*Flowering response time.*—About 8.5 weeks.
*Flowering season.*—Up to 5 weeks or longer.
*Lasting quality* (*shelf life*).—Relatively good, about 28 days.

Foliage:

*Shape.*—Ovate, with straight base, medium expression of lobes, and with acute to acuminate tip.
*Leaf arrangement.*—Alternate.
*Margin.*—Entire.
*Upper leaf surface.*—Smooth and flat texture; only weakly veined, color of veins: RHS 145 A.

*Lower leaf surface.*—Flat and smooth texture, except for the slightly protruding midrib and finer side veins, in a palmate pattern, the vein color is greenish-white, RHS 145 C.

*Leaf blade size.*—Length 14.0 cm. Width 10.2 cm.

*Color.*—Uniform, dark-green green.

*Mature foliage.*—Upper surface RHS 139 A; lower surface, RHS 137 A.

*New foliage.*—Upper surface RHS 144 A to 143 A; lower surface RHS 144 A.

*Leaf petiole.*—Upper surface light green RHS 145 B, no anthocyanin; lower surface greenish-white RHS 145 C.

Petiole: Length 7.5 cm; diameter 3 mm.

Aspect: The petioles are horizontally directed, with the leaf blades horizontally directed or slightly downwards.

Disease resistance: No special observations made.

Flowering description: Whole inflorescence with surrounding bracts: medium sized, mainly horizontally directed, young bracts slightly upward directed; average inflorescence height 40–50 mm.

*Diameter.*—About 26 cm.

*Number of bracts per inflorescence* 9–11 (length over 2 cm).

*Size of largest bracts.*—12.3 cm long, 9.3 cm wide.

*Bract shape.*—Ovate, with an almost straight base, only weak lobes, and with acute to acuminate tip.

*Surface texture.*—Almost flat and slightly rugose (increases with maturing of bracts); the veins are only weakly expressed on the surface, their color corresponds closely to the bract color, the base of the midrib is about RHS 145 B; the veins on the lower surface are slightly protruding, their color is a light, yellowish-green, approximately RHS 150 C, and the base of the midrib RHS 145 A to RHS 145 B, light green.

*Color.*—Generally a light lemon-yellow, uniform; upper surface RHS 4 C lower surface RHS 154 D.

*Petiole.*—Length: 2.0 cm, light green color RHS 145 B.

*Cyme.*—About 10–15 cyathia, in a narrow cluster, about 20 mm wide.

*Cyathium.*—About 50 mm wide, 15 mm long (including peduncle and male lowers ): light grass-green color RHS 143 A to 143 C, the top is a pale yellow, RHS 4 C to RHS 4 D; one nectary per cyathium Nectar Cups: about 50 mm wide, intense yellow, RHS 7 A, no anthocyanin.

Reproductive organs:

*Stamens.*—Quantity: about 20 in a bundle; filament length 3–4 mm; filiform shape; very light yellow, RHS 4 C.

*Pollen.*—Ouantity: moderate; yellow in color, RHS 12 A.

*Pistils.*—Style and stigma color very light yellow, RHS 4 C.

*Ovaries.*—Medium green, RHS 143 A, triangular, 3 ovules.

*Seed set.*—Under the greenhouse conditions described no spontaneous seed set was observed, but fertile when pollinated, shape and development are typical for the species.

I claim:

1. A new and distinct cultivar of Poinsettia plant named 'Fislemon', as described and illustrated herein.

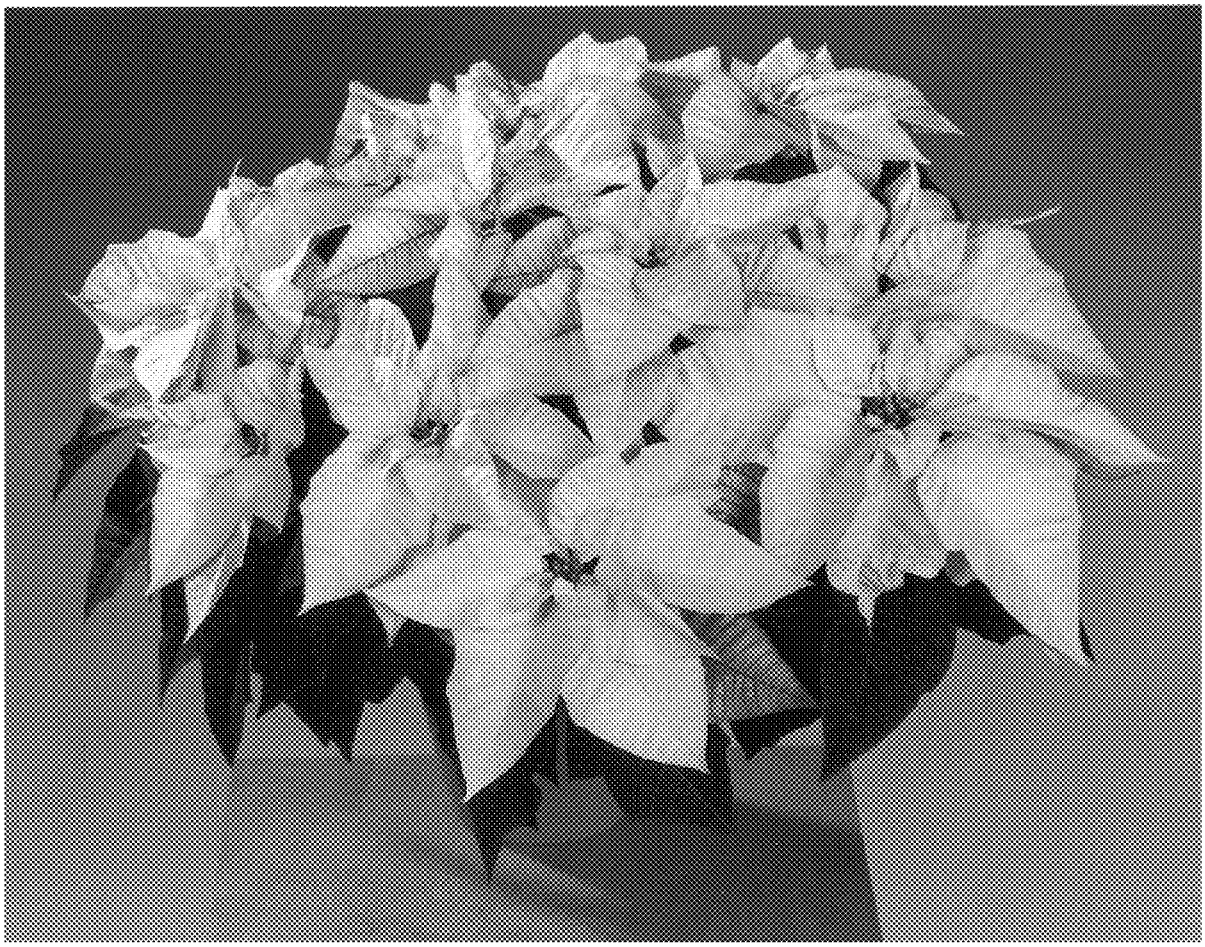

* * * * *